United States Patent
Jann et al.

[11] Patent Number: 5,875,029
[45] Date of Patent: *Feb. 23, 1999

[54] APPARATUS AND METHOD FOR SURFACE INSPECTION BY SPECULAR INTERFEROMETRIC AND DIFFUSE LIGHT DETECTION

[75] Inventors: Peter C. Jann, Santa Clara; Wayne W. Li, Fremont; Igor Iosilevsky, Hayward; Kenneth H. Womack, San Diego; Vlastimil Cejna, Mountain View; George A. Burt, Jr., Fremont, all of Calif.

[73] Assignee: Phase Metrics, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 908,061

[22] Filed: Aug. 11, 1997

Related U.S. Application Data

[63] Continuation of Ser. No. 588,870, Jan. 19, 1996, abandoned.

[51] Int. Cl.⁶ ............................................. G01B 9/02
[52] U.S. Cl. ................... 356/345; 356/351; 356/237.2
[58] Field of Search ................... 356/445, 446, 356/371, 345, 349, 351, 357, 359, 360, 237.2; 250/206.1, 559.09, 559.16, 559.4, 559.45; 369/58

[56] References Cited

U.S. PATENT DOCUMENTS

| | | | |
|---|---|---|---|
| 3,984,189 | 10/1976 | Seki et al. | 356/446 X |
| 4,092,068 | 5/1978 | Lucas et al. | 356/446 X |
| 4,172,666 | 10/1979 | Clarke | 356/446 X |
| 4,412,746 | 11/1983 | Yokouchi | 356/446 |
| 4,589,773 | 5/1986 | Ido et al. | 356/371 |
| 4,622,502 | 11/1986 | Maruo et al. | 250/206.1 X |
| 4,794,264 | 12/1988 | Quackenbos et al. | 356/446 X |
| 4,794,265 | 12/1988 | Quackenbos et al. | |
| 4,832,487 | 5/1989 | Mikuriya et al. | 356/237 |
| 4,844,616 | 7/1989 | Kulkarni et al. | 356/351 |
| 5,270,794 | 12/1993 | Tsuji et al. | 356/446 X |
| 5,389,794 | 2/1995 | Allen et al. | 356/237.2 |
| 5,661,559 | 8/1997 | Brezoczky et al. | 356/359 |
| 5,710,631 | 1/1998 | Bou-Ghannam et al. | 356/351 |

*Primary Examiner*—Samuel A. Turner
*Attorney, Agent, or Firm*—Blakely, Sokoloff, Taylor & Zafman

[57] ABSTRACT

A simple yet versatile noncontact optical inspection instrument and method are described for the inspection of magnetic disk surfaces for surface defects. This instrument is capable of inspecting the disk surface at any point in the disk manufacturing process. Surface defects such as bumps, pits and scratches can be measured. Surface contaminants such as particles and stains can also be measured. The instrument is also capable of discriminating between surface defects and surface contaminants. The instrument is comprised of two identical optical sensors which are located on opposite sides of the disk. A carriage supports and translates these sensors along the disk radius while a spindle rotates the disk. Both surfaces of the disk are therefore simultaneously scanned in a spiral fashion. The sensor's illumination optics produce a monochromatic focused spot of light which is normally incident upon the disk surface. The sensor uses two collection optics channels which simultaneously detect both the specular reflected light and the diffuse scattered light produced by the disk surface. Both the angle and power of the specular reflected light are measured, while just the power of the diffuse scattered light is measured. The output signals from the sensors are processed to estimate the size of the defects and to determine the type of defect.

14 Claims, 9 Drawing Sheets

APPARATUS AND METHOD FOR SURFACE INSPECTION BY SPECULAR INTERFEROMETRIC AND DIFFUSE LIGHT DETECTION

This is a continuation application of application Ser. No. 08/588,870, filed Jan. 19, 1996 and now abandoned.

FIELD OF THE INVENTION

The invention relates to an optical detection system and method for detecting defects on a smooth surface, and more particularly for detecting surface defects on the surface of a magnetic disk.

BACKGROUND OF THE INVENTION

There is a significant quality control problem associated with surface imperfections on magnetic disks. This typically occurs, for example, on nickel-plated aluminum substrates used in the manufacture of thin-film magnetic media, but may be a problem with respect to any area where a smooth surface is desired. Typical surface defects include pits, dirt, dust, oil, stains, fingerprints and the like. Defects on the surface of rigid magnetic media are often a result of an impingement onto the surface or a tearing of material away from the surface. These types of defects can be very large scratches or gouges on the surface or very small (5 um and smaller) tears or pricks on the surface. The large surface defects, because of their size and scattering properties, are readily distinguishable through sophisticated data processing performed on light reflected from the surface of the medium under test by an inspection apparatus which includes a light source directed at the disk. Small surface defects (5 um and smaller) have not been so readily detectable, and even when detected, have been difficult to identify and classify. For example, the systems described in U.S. Pat. Nos. 4,794,264 and 4,794,265, entitled "SURFACE DEFECT DETECTION AND CONFIRMATION SYSTEM AND METHOD" and "SURFACE PIT DETECTION SYSTEM AND METHOD", respectively, issued to Quackenbos et al. describe systems for detecting pits on a smooth surface by irradiating an area of the surface. Two sensors separately detect radiation scattered from the surface. One sensor detects radiation scattered in a near-specular region (40–100 milliradians or 2.29–5.73 degrees), while a second sensor detects radiation scattered in a far-specular region (greater than 100 milliradians or 5.73 degrees). The near-specular signal is normalized with respect to the far-specular signal to indicate a pit. The Quackenbos devices lack any ways to distinguish between a surface depression, i.e., a pit, and a surface protrusion, i.e., a bump. Quackenbos does not distinguish surface protrusions of a smooth nature (i.e., bumps) from more jagged contaminants. Quackenbos also makes the assumption that surface depressions or "pits" do not have far-specular reflection patterns, which has proved to be a limiting and problematic assumption. Additionally, the Quackenbos devices lack any means to determine the slope of the defect from which the light has scattered.

Thus, there is a need in the magnetic disk drive industry for a noncontact optical inspection instrument which is capable of detecting defects in the surfaces of polished magnetic disk substrates. This instrument must be sensitive, fast and inexpensive and must be capable of detecting surface defects and estimating the size of these defects. This instrument must also be able to distinguish between various kinds of defects such as bumps, pits and scratches and also between these defects and surface contaminants such as particles and stains. The instrument should also be able to determine the slope of the defect from which the light has scattered.

SUMMARY OF THE INVENTION

The present invention is a simple, yet versatile noncontact optical inspection instrument and method for the inspection of magnetic disk surfaces for surface defects. This instrument is capable of inspecting the disk surface at any point in the disk manufacturing process. Surface defects such as bumps, pits and scratches are measured. Surface contaminants such as particles and stains can also be measured and quantitatively characterized. The instrument is also capable of discriminating between surface defects and surface contaminants and between pits and bumps.

In one embodiment, the instrument includes an optical sensor which is mounted on a carriage which supports and translates the sensor along the disk radius while a spindle rotates the disk. Illumination optics produce a monochromatic focused spot of light which is normally incident upon the disk surface. The sensor includes four collection optics channels which simultaneously detect both specular reflected light and diffuse scattered light produced by the disk surface. Both the reflection angle and power of the specular reflected light are measured, while just the power of the diffuse scattered light is measured.

The specular channel employs a quadrant photo-diode to obtain information about the reflection angle of the returned light, which is correlated with the slope of any defect present on the disk under inspection. In another embodiment, interferometric techniques are used in the specular channel to estimate the height of defects above the surface of the disk. Both equal-length and unequal-length interferometers may be used to sense defects in this embodiment. The output signals from the sensor are then processed to estimate the size, shape and depth of the defects and to determine the type of defect.

The magnetic disk substrate which is being inspected may be held by a vacuum chuck and rotated by an air bearing spindle. Two diametrically opposed non-contact optical sensors may be simultaneously radially translated over each of the disk surfaces by the carriage, thereby producing spiral shaped inspection scans of both surfaces of the disk. These scans consist of adjacent tracks which may or may not overlap depending upon the throughput and precision required of the tool.

A variety of substrate materials may be examined using the method and apparatus described herein. These and other characteristics of the present invention will become apparent through reference to the following detailed description of the preferred embodiments and accompanying drawings.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

A surface inspection apparatus and method is described. In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

Figure 1:
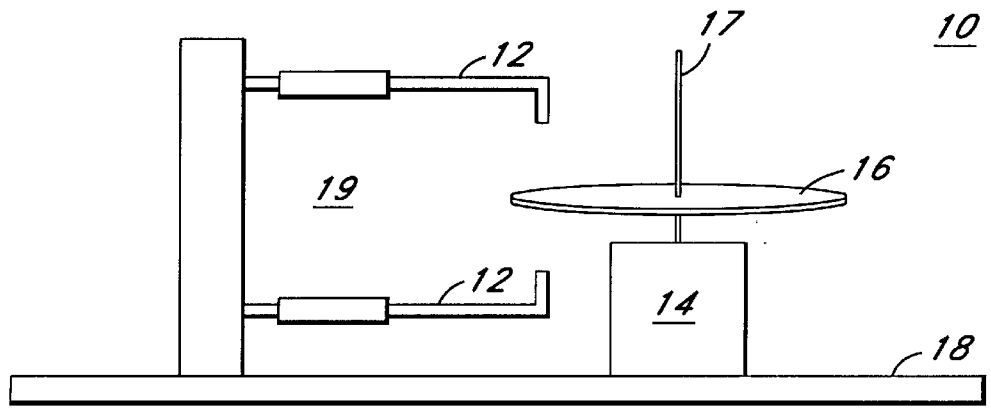
FIG. 1 illustrates generally a system for inspecting disk surfaces according to the present invention.

As shown in FIG. 1, the surface inspection apparatus of the present invention, generally illustrated at 10, comprises dual sensors 12 mounted on a carriage 14 and situated in relation to a magnetic disk substrate 16 such that one sensor monitors a first surface of the disk 16 while the other sensor monitors of a second surface of the disk 16. The magnetic disk substrate 16 is rotated about an axis 17 during operation of the inspection apparatus. The carriage 14 is preferably movable along a track 18 so that the inspection apparatus of the present invention can be used to produce a scan of an entire disk as the carriage 14 is translated along the radius of the disk 16 as it is rotated. Each of the sensors 12 is capable of distinguishing bumps, pits and scratches from surface contamination and quantitatively characterizing the geometry of the former while providing information regarding their location on the medium being examined.

Figure 2:
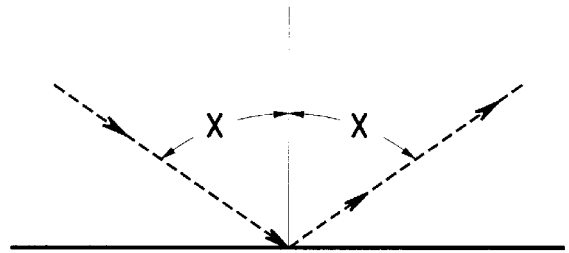
FIG. 2 illustrates specular reflection from a smooth surface employed by the present invention to sense the slope and magnitude of a defect on a disk under examination.
Figure 3A:
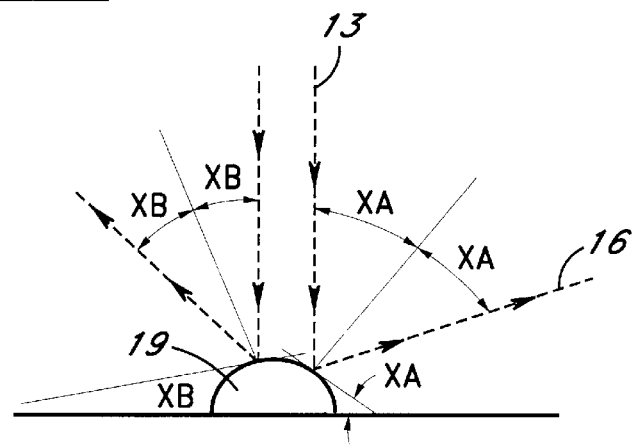
FIGS. 3A and 3B illustrate the geometrical principles of diffuse reflection of an incident light beam from a surface.
Figure 3B:
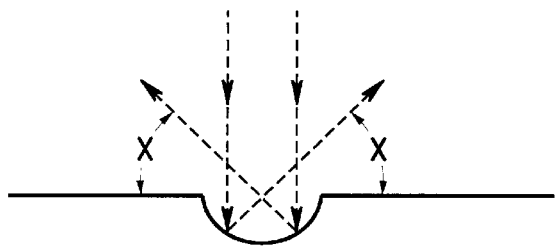

The physical principles employed by the present invention to sense defects in the disk 16 under examination are shown schematically in FIGS. 2 and 3. The sensors 12 use two forms of light reflected from the disk 16 to characterize defects. The first form of reflected light is specularly reflected from smooth regions of the disk, as illustrated in FIG. 2. The sensor 12 shines an incident beam of light 13 at the disk 16 under examination. The light beam 13 is preferably incident at a normal or near-normal angle to the plane of the disk 16. If the surface of the disk 16 has a defect which imparts a local non-zero slope to the disk, the beam 13 will be reflected specularly according to the law of reflection at an angle X equal to the angle the beam 13 makes with the extended local normal 15 of the disk. The angle X that the local region of the disk surface 16 makes with the plane of the disk surface can therefore be directly measured by determining the angle made by the specularly-reflected beam. The sensor 12 also uses diffusely-reflected light to sense particles and other small defects which scatter incident light from the surface of the disk. In FIGS. 3A and 3B, the incident beam 13 is incident on a region of the disk 16 which contains a small defect 19 or pit 11. The small defect 19 or pit 11 scatters the incident light in many directions simultaneously. This diffusely-scattered light is detected by the sensor 12 to characterize defects which do not specularly reflect incident light, such as dirt particles or other small irregularities on the surface of the disk 16. The sensor 12 is illustrated in more detail in FIG. 4.

Figure 4:
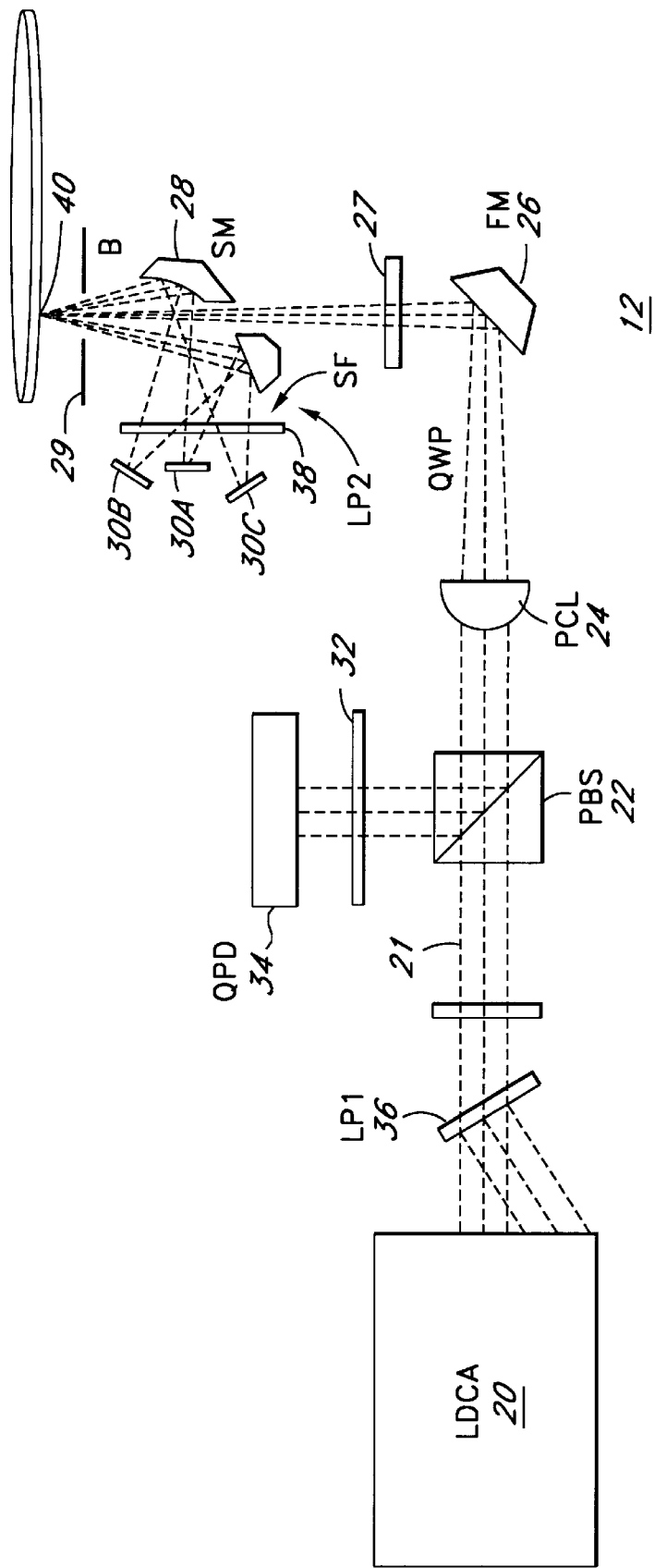
FIG. 4 is a schematic illustration of a first embodiment of the disk inspection system of the present invention.

Reference is now made to FIG. 4. Since the two sensors 12 shown in FIG. 1 are substantially the same, only one will be shown from hereon to avoid unnecessary duplication. It is to be understood that two or more sensors may be employed. The sensor 12 includes a laser diode collimator assembly (LDCA) 20, a first linear polarizer 36, a polarizing beamsplitter 22, a plano-convex lens 24, a flat mirror 26, a quarter-wave plate 27, a spherical mirror with center hole 28, a baffle 29, a spatial filter in the form of an opaque slit, a second linear polarizer 38, a photomultiplier tube assemblies 30A, 30B, and 30C, and a quadrant photo-diode 34.

The sensor assembly 12 operates as follows. The collimated output beam 21 of the laser diode collimator assembly (LDCA) 20 propagates along an optical path which includes: first linear polarizer 36, polarizing beamsplitter 22, plano-convex lens 24, flat mirror 26, quarter-wave plate 27, spherical mirror 28 and baffle 29. The collimated output beam 21 is brought to a focus on the surface of the magnetic disk substrate 16 to form an illumination spot 40. Typically, the disk illumination spot 40 is about 22 um in diameter, has a numerical aperture of 0.03, is circularly polarized, has a wavelength of 670 nm and is normally incident upon the surface of the disk 16. The small numerical aperture precludes the need for a focus servo subsystem to accommodate any disk axial run-out, while the laser diode collimator assembly includes an output power servo circuit to stabilize the assembly's output.

As the surface of the magnetic disk substrate 16 moves through the focused illumination spot 40, two kinds of reflected light are produced from the surface 16, as described above. The first kind of light is a specular reflected beam which is circularly polarized and propagates along an optical path which includes: baffle 29, spherical mirror 28, quarter-wave plate 27, flat mirror 26, plano-convex lens 24 and polarizing beamsplitter 22 to the quadrant photo-diode (QPD) 34. Quadrant photo-diode (QPD) 34 comprises four independent photo-diodes which will be described in more detail below. Slope or tilt in the disk surface, due to surface defects or axial run-out, effects the position on the quadrant photo-diode 34 whereupon the specular reflected beam is incident. By properly processing the signals produced by the four photo-diode sections comprising the quadrant photo-diode 34, the position of the specular reflected beam upon the quadrant photo-diode 34 can be determined. Using this positional information, the slope of the surface of magnetic disk substrate 16 at the location from which the specular reflected beam originated can be measured over a range of ±0.01 to 0.86 degrees. The techniques employed by the present invention to process the output of the quadrant photo-diode 34 will be described in greater detail below. Bumps, pits and scratches can be detected and bumps can be distinguished from pits by measuring the polarity of the processed signals. The relative specular reflectance of the disk surface is also measured, to permit surface stain inspection, by measuring the sum of the signals produced by the four photo-diodes. Finally, the use of normal incidence illumination eliminates sensing ambiguity between disk surface slope and height.

The second kind of reflected light which is produced by the disk surface is a diffuse, highly divergent, diffracted or scattered beam which is elliptical polarized and is collected by the spherical mirror 28. The spherical mirror 28 reflects this light onto the photomultiplier tube (PMT). Extremely small surface defects and surface contaminants on the disk 16 such as particles produce this scattered light. In the described embodiment, the spherical mirror can collect light over a numerical aperture of 0.06–0.40 in the plane of the diagram and 0.06–0.47 in the plane normal to the diagram which, in combination with an illumination spot diameter of about 20 um, permits the detection of defects and particles of sub-micron sized geometries. The photomultiplier tube output signals will therefore consist of pulses, as these defects or particles pass through the focused illumination spot, whose amplitudes are proportional to the size of the defects.

Figure 5:
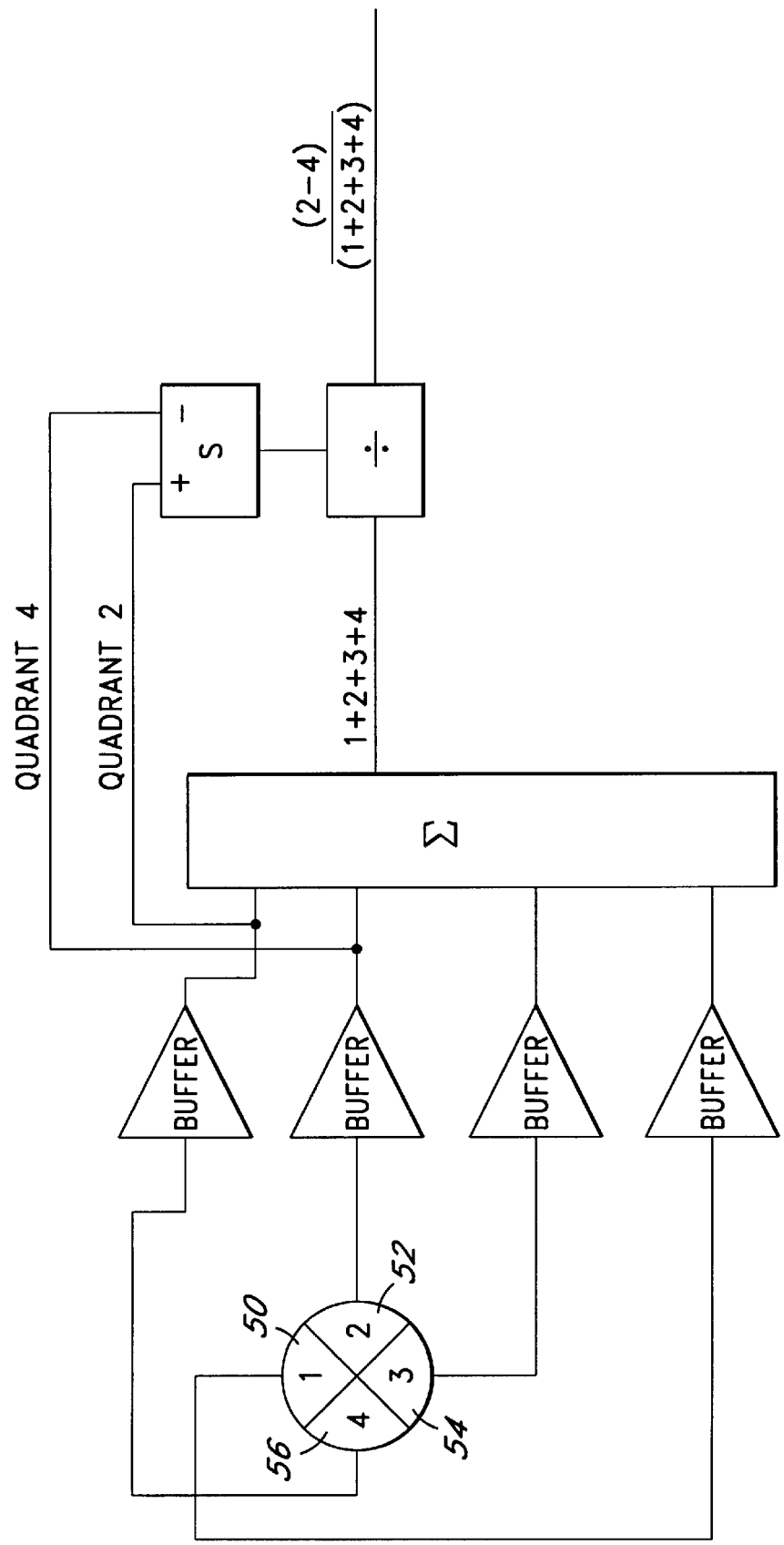
FIG. 5 is a schematic diagram illustrating a method employed by the present invention for calculating the slopes of defects on a disk.

FIG. 5 illustrates a signal processing technique that may be employed in accordance with the present invention for processing the output signals of the quadrant photo-diode 34. The quadrant photo-diode 34 has four photo-diodes 90, 92, 94 and 96, each of which produces an output voltage indicative of the intensity of the light incident on its individual surface. When quadrants 1 and 3 are aligned to be parallel with the disk's redial or tracking axis, the signal voltage (2–4)/(1+2+3+4) will be proportional to the slope of the disk surface along the azimuth or scanning axis. In this equation, the numerals 1, 2, 3, and 4 represent the signal received at the corresponding quadrant of the quadrant photo-diode. The polarity of these signals indicates whether the voltage slope is ascending or descending, thereby permitting distinction between bumps and pits. Normalization by division of the signal by the summed–(1+2+3+4) eliminates errors caused by changes in the laser diode collimator assembly 20 output power and by changes in the disk surface 16 specular reflectance. As is shown in FIG. 5, the four quadrants receive light at different times, according to the direction in which the reflected beam of light is moving. Quadrants 1 and 3 receive light along the tracking axis, while quadrants 2 and 4 receive light along the scanning axis.

Figure 6:
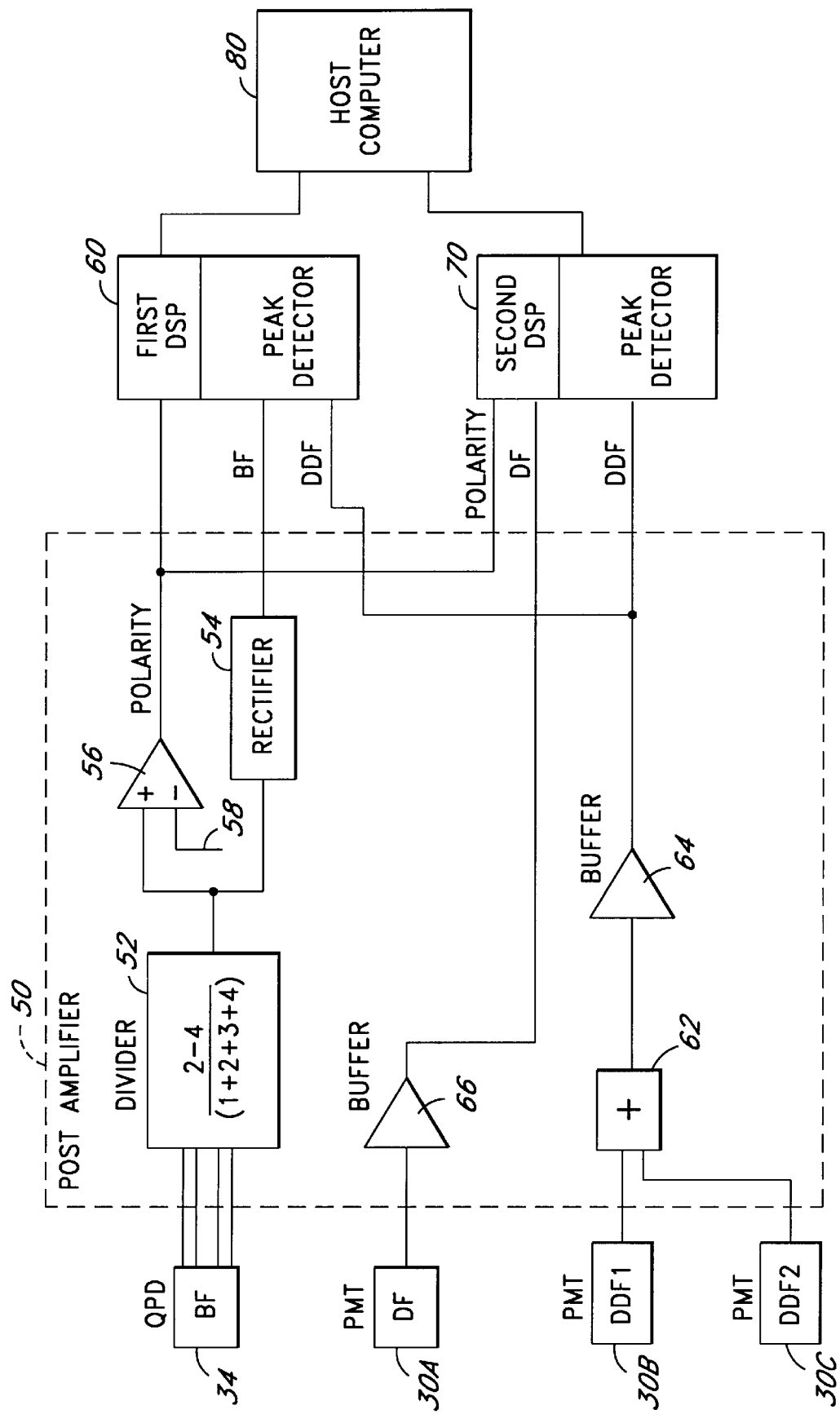
FIG. 6 is a schematic of a signal processing technique used to detect and classify defects of the present invention.

Referring now to FIG. 6, a system level block diagram of the signal processing aspects of the present invention is shown. The quadrant photo-diode 34 produces four signals, each signal corresponding to the intensity or power of the light received at one of the quadrants associated with the specular or bright field channel. The signals are provided to a post amplifier 50. Similarly, the three photomultiplier tube signals corresponding to the diffuse or dark field channel 30A, the first double dark field 30B, and the second double dark field 30C are provided to the post amplifier 50. Within the post amplifier 50, the four signals of the bright field channel are provided to a divider 52 that contains adders and dividers, producing a signal proportional to the difference between the second and fourth quadrant signals and inversely proportional to the sum of all four quadrants. The output of the divider 52 is provided to a rectifier 54, that produces a positive-only signal proportional to the magnitude of the output of the divider 52. To retain the polarity or sense of the output of the divider 52, the signal is also provided to a comparator 56, which provides a polarity signal indicative of whether the divider 52 output exceeds a threshold level 58. The threshold level is ordinarily selected to be slightly greater than the maximum expected noise level, and thus provides both a magnitude and a polarity indication. The comparator output and the rectifier output is provided to a first digital signal processor 60, and the comparator output is provided to a second digital signal processor 70, both containing a peak detector.

In parallel with the processing of the bright field channel, the two double dark field channels 30B and 30C are provided to the post amplifier 50, wherein they are added together 62 and buffered 64, the buffer output being provided to the second digital signal processor 70. Similarly, the dark field channel 30A is buffered 66 and provided to the second digital signal processor 70. Both digital signal processors contain a peak detector having a sensitivity determined by an external host computer 80.

Referring now to FIGS. 5 and 6, the first digital signal processor 60 determines whether light reflected from the disk surface 16 has varied from the normal direction by more than a predetermined level and, if so, in which direction. If the specularly reflected light falls on the second quadrant 92 of the bright field quadrant photo-diode 34 before falling on the fourth quadrant 96, or vice versa, the shape of the defect can be determined. Thus, the first digital signal processor can distinguish concave regions from convex, thus distinguishing pits from bumps. The slope of the defect is determined by the rectifier signal, which is proportional to the difference between the two quadrant photo-diode amplitudes.

When a defect has sufficient jaggedness, light reflecting from or scattered by the defect travels at a large angle with respect to the normal of the disk. When a defect is encountered having sufficient jaggedness, as when a very small particle is encountered, or the sharp bottom of a pit, or when a bump comes to a point, the reflect light scatters diffusely and is detected by the double dark field channels. Thus, the second digital signal processor distinguishes highly jagged events such as particles from smoother defects such as bumps. The threshold level is determined by the host computer, which can set the sensitivity levels of the two signal processors.

The signal processor illustrated in FIG. 5 forms the signal (2–4)/(1+2+3+4) with the use of adders and dividers. Each of the output signals from the photo-diodes 90, 92, 94, and 96 is fed to a corresponding preamplifier 91, 93, 95 and 97, respectively. The output from each of these preamplifiers is then fed to an adder circuit 68, which combines them to form the denominator signal 1+2+3+4. The numerator signal (2–4) is formed by combining, respectively, the output of preamplifiers 93 and 97 at a second adder 99. Division circuit 72 processes the signal outputs from the addition circuits 68 and 99 to form the signal output (2–4)/(1+2+3+4). This output is then fed to a processing logic and further processed as will be described below.

Bumps, pits and scratches can also be reliably detected on textured disk surfaces by using either quadrant pairs 1 and 3 or 2 and 4 depending upon which pair is not illuminated by the typical "bow-tie" shaped diffraction pattern which is produced by the surface texture. The major axis of this diffraction pattern has been observed to typically lie along the disk surface radial axis. Quadrant pair 2 and 4 is therefore not illuminated or "blinded" by this diffraction pattern, thereby permitting the use of the signal voltage (2–4)/(1+2+3+4) for reliable large defect detection on textured disk surfaces.

A system computer 80 of the embodiment shown in FIG. 6 is advantageously utilized to distinguish between disk surface defects, such as bumps, pits and scratches, from surface contaminants such as particles, by using a "global" signal processing technique which simultaneously monitors the outputs from the above described "local" algorithms for the quadrant photo-diode 34 and the photomultiplier tubes 30A, 30B, and 30C shown in FIGS. 5 and 6, respectively. The host computer 80 may collect information from a plurality of sensors, and may interface with memory or other processors.

Alternate embodiments of the present invention are illustrated in FIGS. 7–10. In these embodiments, the non-specular channel of the defect detector is the same as that of the first embodiment described above. However, in these embodiments, interferometric techniques are used in the specular channel to sense changes in the height of the disk surface, thereby allowing extremely accurate measurement of defects on the surface of the disk 16.

Figure 7:
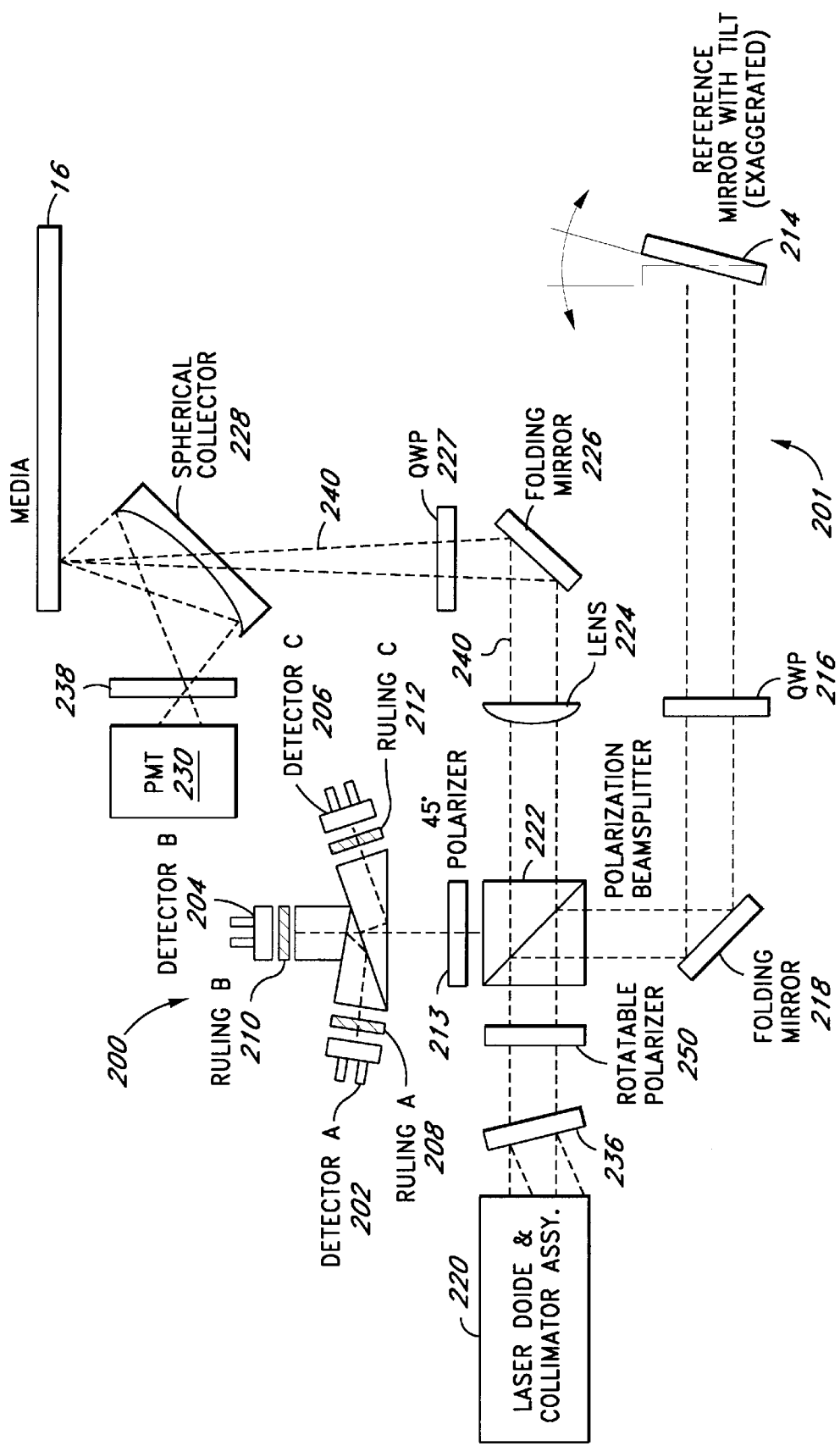
FIG. 7 is a diagram of an alternate embodiment of the present invention employing an equal path-length interferometer in the specular channel of the disk inspection apparatus to measure defects on the surface of the disk.

The first alternate embodiment of the present invention illustrated in FIG. 7 differs from the above-described first embodiment in the addition of a reference arm 201 for the return light path and the replacement of the quadrant photo-diode 34 with a 3 detector prism assembly 200. The detector assembly 200 includes three detectors 202, 204 and 206. Immediately in front of each detector are 50% duty cycle rulings 208, 210 and 212, respectively. The detector prism assembly 200 also includes a 45-degree polarizer 213 and a prism 215.

Each of the rulings 208, 210 and 212 is illuminated by a high density straight line interference fringe pattern having the same nominal period and orientation as the three rulings. The high density fringe pattern is obtained by tilting a reference mirror 214 on the reference arm 201. The mirror tilt can be adjusted once and locked down. The reference arm 201 additionally includes a quarter-wave plate 216 and a folding mirror 218. The reference arm 201 receives light from a system LDCA 220 analogous to that described in the first embodiment. The light originating from the LDCA 220 is then reflected from an analogous polarization beamsplitter 222 into the reference arm 201. This light is then reflected from the reference mirror 214 and re-reflected on the mirror 218, to be incident on the detector prism assembly 200. The other components of the system are analogous to those of the embodiment of the invention illustrated in FIG. 4 and include a linear polarizer 236, a lens 224, a folding mirror 226, a quarter-wave plate 227, a spherical collector 228, a linear polarizer 238 and a photomultiplier tube 230.

The three rulings 208, 210 and 212 differ in their phase relationship with respect to the illuminating interference pattern. They are each shifted laterally by an amount corresponding to 90 degrees. As the media 16 surface height changes, the interference pattern shifts laterally across each of the rulings 108, 110 and 112, yielding sinusoidal detector signals that are delayed in phase by 90 degrees with respect to one another. The surface height of the disk 16 averaged over the laser spot size at the media is computed in real time by the system computer using the expression:

$$h = \frac{\lambda}{4\pi} \arctan\left[\frac{C-B}{A-B}\right]$$

where h is the surface height, $\lambda$ is the wavelength of light emitted from the LDCA 120 (670 nm in the presently-preferred embodiment), and A, B and C are the output signals from each of the detectors 202, 204 and 206 processed by familiar methods well known to those skilled in the art. The length of the reference arm 201 in this embodiment is chosen to be equal to the length of the test arm, which is the light path 240 from the LDCA 220 to the medium 16 and to the detector assembly 200, in order to accommodate frequency drift of the laser diode 220. An important advantage of such an equal-path length interferometer configuration is that it obviates the need for a frequency-stabilized light source. A rotatable polarizer 236 located between the polarization beamsplitter 222 and the laser 220 can be rotated and locked in position. It therefore provides a convenient method for controlling the relative amounts of light entering the test and reference arms. In this way, the interferometer can be adjusted for 100% interference contrast regardless of the reflectivity of the media.

The above-described alternate embodiment is advantageously relatively immune to spurious interference patterns due to imperfect anti-reflection coatings on the system optics, since sources of interference noise must have spatial frequencies comparable to the rulings to impact surface height measurements made by this embodiment of the invention. An additional advantage of this embodiment is that it provides direct surface height data with a height resolution of 1 nanometer rms assuming a signal-to-noise at the detectors of 100, which can be achieved with the components described above. This surface height data gives a quantitative map of the surface of the disk 16 under inspection, thereby allowing an extremely accurate characterization of the disk surface.

It should be understood that similar interferometers can be set up with 4 detectors instead of 3. Indeed, in general, N detectors may be used with an appropriately designed arctangent algorithm. It should also be recognized that a variety of multiple detector prism and beamsplitter assemblies are also possible for directing the beam to all detectors. It should also be understood that no prism assembly at all is needed in the above-described embodiment if a specially fabricated phase-shift ruling pattern is inserted directly in front of a multiple segment detector array.

Figure 8:
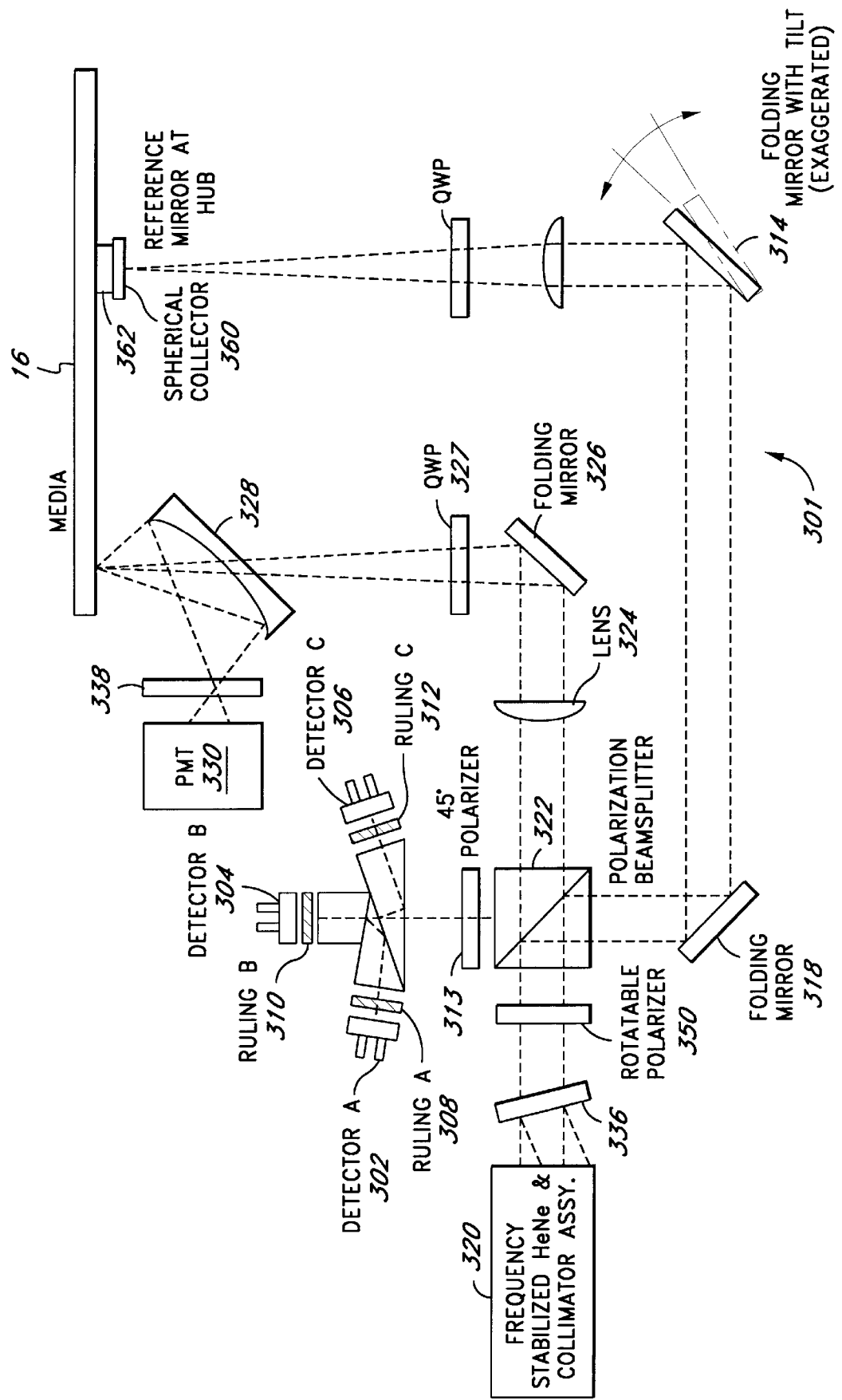
FIG. 8 is a diagram of a second alternate embodiment of the present invention employing an unequal path-length interferometer and hub reference mirror in the specular channel of the disk inspection apparatus to measure defects on the surface of the disk.

A second alternate embodiment of the present invention, employing an unequal-length interferometer with a frequency-stabilized light source, is illustrated in FIG. 8. Components analogous to those illustrated in the embodiment of FIG. 7 are numbered analogously. The second alternate embodiment differs from the first in that a reference mirror 360 is provided that is mechanically connected to the spindle motor shaft 362 or housing or mount. Additionally, because the interferometer employed is an unequal-path interferometer, the light source is frequency stabilized and is preferably a frequency-stabilized HeNe laser with a collimator assembly.

Figure 9:
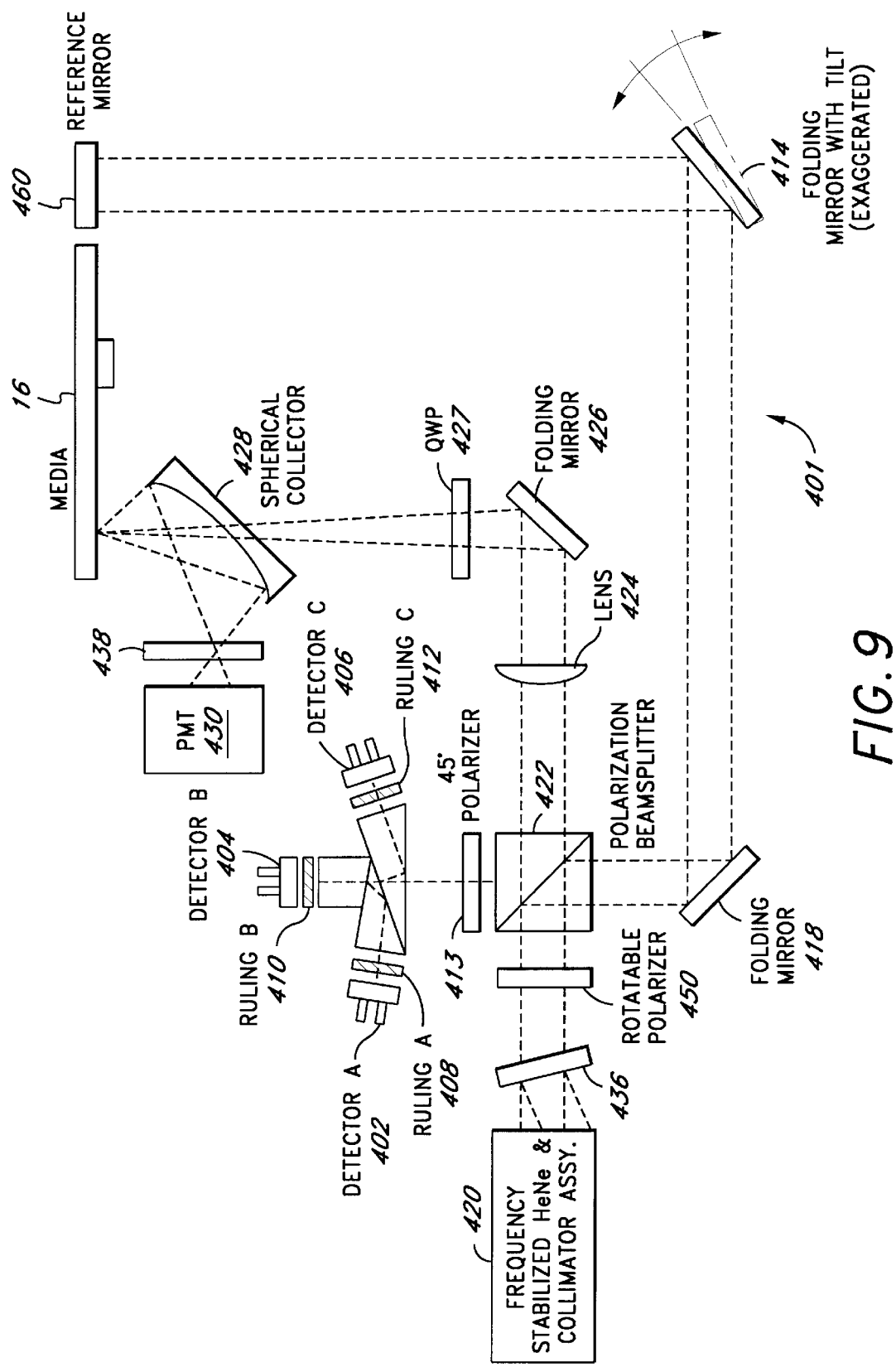
FIG. 9 illustrates a modification of the embodiment of FIG. 8 including a fixed reference mirror adjacent to the disk under test.

An additional location for the reference mirror in an unequal-path length system is illustrated in FIG. 9, which depicts an embodiment with the reference mirror 460 located adjacent to the disk 16 under examination. This embodiment functions in all other ways identically to that illustrated in FIG. 8, and analogous components are numbered analogously. The placement of the reference mirror 460 in the embodiments of FIGS. 8 and 9 is advantageous in that the reference arm 460 experiences the same or nearly the same vibration and drift as the test arm.

Figure 10:
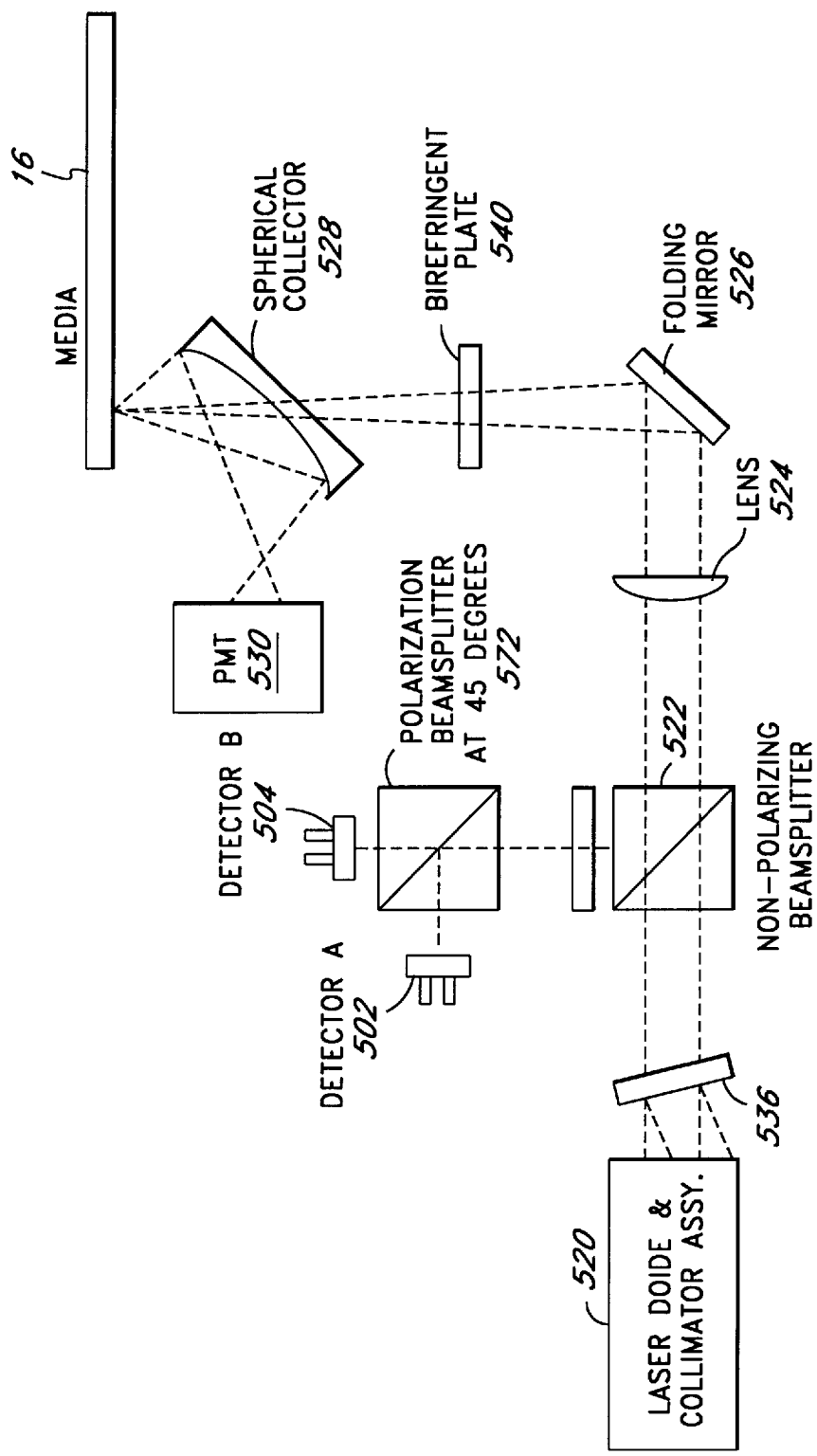
FIG. 10 illustrates a third alternate embodiment of the present invention incorporating a Nomarski interferometer and a birefringent plate.

A third alternate embodiment of the invention which includes a Nomarski interferometric specular channel is illustrated in FIG. 10 and incorporates a birefringent plane parallel plate 570 in the focused beam. While the plate 570 is shown in FIG. 12 as being located between the folding mirror 526 and the spherical collector 528, it should be understood that it could equally well be located between the beamsplitter 522 and the focusing lens 524. The embodiment of FIG. 10 includes a nonspecular channel which functions identically to those described above.

The plate 570 is designed to achieve a desired shear (spatial separation) between two focal spots it creates at the media surface. The amount of shear is chosen to lie in the range of a few microns to approximately half the width of the focal spot in this embodiment. The shear distance is kept small enough that double signals are not generated in the nonspecular channel for small scattering defects. The embodiment illustrated in FIG. 10 includes a polarization beamsplitter 572 so that interference signals obtained at the two detectors 502 and 504 are 180 degrees out of phase. As the surface height changes at the media 16, due to the aforementioned phase difference one detector signal increases while the other decreases. The ratio of the difference divided by the sum of the respective detector signals provides a signal that is linearly proportional to the surface slope of the media 16 independently of changes in laser output or changes in surface reflectivity. Integration of the slope signal as described above provides data directly proportional to surface height. This technique is extremely sensitive, permitting detection of height changes as small as 5 angstroms. The slope signal generated in this embodiment is processed as described above for the first embodiment and is also thresholded to detect the occurrence of a defect and integrated to obtain surface height only the vicinity of each defect.

It will be understood that the apparatus and method of the present invention for sampling defects in a medium may be employed with any plateshaped medium including compact disks or plate-shaped metal surfaces which require finishing to extremely close tolerances. It may also include any interferomeric technique in the specular channel.

Thus, there are numerous other embodiments of the defect detection system of the present invention which will be obvious to one skilled in the art, including but not limited to changes in the dimensions of the optical path, the type of optical elements, the location and type of detectors, the number of detectors and optical elements, etc. Additionally, one skilled in the art will realize that a noncoherent light source could be used in place of a coherent one. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Figure 11:
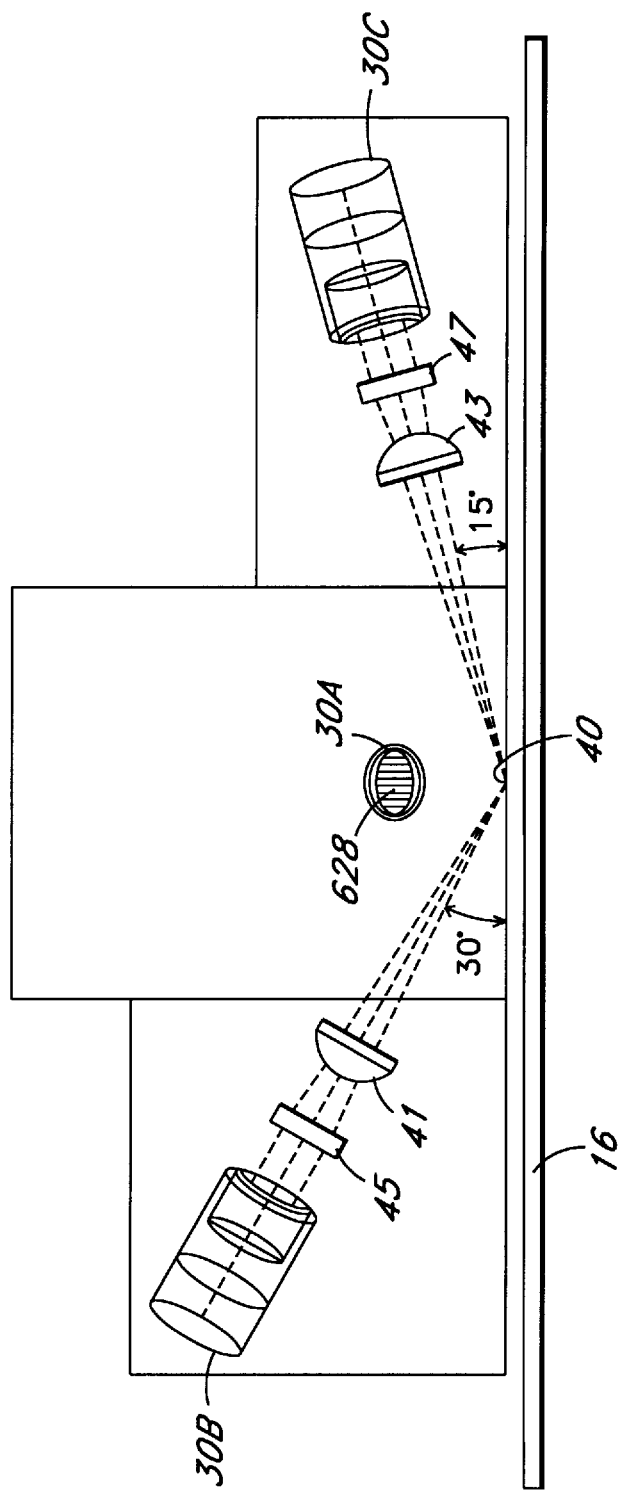
FIG. 11 shows the function and operation of the double dark field channel in one embodiment of the present invention.

Referring now to FIG. 11, a cut away representation of one embodiment of the present invention is shown. A substrate 16 in a horizontal plane is illuminated by the columnated beam of light at an illumination point 40. The beam of light passes through a hole in a circle mirror and illuminates an illumination point 40 on the disk 16. As stated above, the bright field reflection passes through the same hole in the same circle mirror 628, and the dark field channel reflects from the surface of the spherical mirror 628 into the photomultiplier tube 30A. As shown in FIG. 11, however, two additional photomultiplier tubes, 30B and 30C, receive a first double dark field and a second double dark field reflection, respectively. The light received by the first double dark field (DDF) photomultiplier tube (PMT) 30B, and by the second double dark field photomultiplier tube 30C is not reflected from the spherical mirror, nor does it pass through the hole therein, but rather is reflected directly from the illumination point 40. The light reflecting from a sufficiently jagged defect propogates from the reflection point 40 along an optical path which includes: a plano-convex lens 41 or 43, a second linear polarizer 45 or 47, and a double dark field (DDF) photomultiplier tube 30B or 30C. The piano-convex lens 41 or 43 is located such that the distance from the reflection point 40 to the plano-convex lens 41 or 43 is the focal length of the plano-convex lens. The double dark field PMT's collect light at a numerical aperture of 0.1. The first double dark field photomultiplier tube 30B is located at an elevation of 30° from the surface of the disk 16, while the second double dark field PMT 30C is located at an elevation of 15°. Both DDF PMTs are located at an azimuthal angle of 30°, and have a numerical aperture of 0.1.

Light reflecting from the illumination point at an angle sufficient to direct the reflected light into either of the DDF PMTs passes first through a plano-convex lens (not shown) and then through a linear polarizer (not shown) before arriving at the PMTs 30D and 30C, respectively.

We claim:

1. An apparatus for detecting defects on a rotating surface, comprising:

a light source that emits a light beam that is specularly reflected from the rotating surface;

a reflective reference surface that reflects a portion of the emitted light beam to interfere with the specularly reflected light;

a plurality of specular light detectors that detect the light that is reflected from the rotating and reflective reference surfaces, each of said specular light detectors providing a signal representative of the corresponding detected substantially specularly reflected light; and a circuit coupled to the plurality of specular light detectors that normalizes the signals provided by said specular light detectors.

2. The apparatus as recited in claim 1, wherein at least two of said plurality of specular light detectors detect substantially specularly reflected light in a predetermined direction to provide a signal representative of substantially specularly reflected light in the predetermined direction, and said circuit normalizes said signal with a sum of the signals provided by the plurality of specular light detectors.

3. The apparatus as recited in claim 1, wherein said plurality of specular detectors are located to receive light that is reflected within a range that is less than or substantially equal to 2° from a normal to the surface.

4. The apparatus as recited in claim 1, wherein said plurality of specular detectors are located to receive light that is reflected with a range that is less than or equal to 1.72° from a normal to the surface within a single sensor.

5. The apparatus as recited in claim 1, wherein said plurality of specular detectors are located within a single sensor.

6. The apparatus as recited in claim 5, wherein said single sensor is a quadrant photodiode.

7. The apparatus as recited in claim 1, further comprising a diffuse light detector that detects light that is scattered from the surface.

8. A method for detecting defects on a rotating surface, comprising the steps of:

reflecting a light beam from the rotating surface and a reflective reference surface wherein the light reflected from the rotating and reflective reference surfaces interfere;

detecting light that is substantially specularly reflected from the rotating surface and the interfering light reflected from the reflective reference surface with a plurality of specular light detectors, each of said specular light detectors providing a signal representative of the corresponding detected substantially specularly reflected light; and normalizing the signals provided by said specular light detectors.

9. The method as recited in claim 8, wherein the step of detecting light further comprises the steps of detecting light that is substantially specularly reflected in a predetermined direction and providing a first signal representative of light that is substantially specularly reflected in the predetermined direction; and wherein in the step of normalizing, said first signal is normalized with a sum of the signals provided by the plurality of specular light detectors.

10. The method as recited in claim 8, further comprising the step of locating a plurality of specular detectors to receive light that is reflected from the disk within a range that is less than or substantially equal to 2° from a normal to the surface.

11. The method as recited in claim 8, further comprising the step of locating a plurality of specular detectors to receive light that is reflected from the disk within a range that is less than or equal to 1.72° from a normal to the surface.

12. The method as recited in claim 8, further comprising the step of providing a single sensor for detecting light that is substantially specularly reflected.

13. The method as recited in claim 8, further comprising the step of providing a quadrant photodiode for detecting light that is substantially specularly reflected.

14. The method as recited in claim 8, further comprising the step of detecting light that is scattered by the surface.

* * * * *